United States Patent [19]

Gravely et al.

[11] 4,011,141
[45] Mar. 8, 1977

[54] PROCESS FOR MAXIMIZING THE GROWTH AND NICOTINE DEGRADING ACTIVITY OF MICROORGANISMS

[75] Inventors: Lawrence E. Gravely, Louisville, Ky.; Vernon L. Geiss, Floyd Knobs, Ind.; Richard P. Newton, Louisville, Ky.

[73] Assignee: Brown & Williamson Tobacco Corporation, Louisville, Ky.

[22] Filed: Nov. 17, 1975

[21] Appl. No.: 632,857

[52] U.S. Cl. .................................. 195/96; 195/2; 195/51 R; 131/141
[51] Int. Cl.² .......................................... C12B 1/20
[58] Field of Search ............... 195/27, 96, 2, 51 R; 131/141

[56] References Cited
UNITED STATES PATENTS

| | | | |
|---|---|---|---|
| 2,149,179 | 2/1939 | Moser | 195/27 |
| 3,132,651 | 5/1964 | Kiefer | 195/2 UX |
| 3,747,608 | 7/1973 | Gravely et al. | 131/141 |

*Primary Examiner*—Alvin E. Tanenholtz
*Attorney, Agent, or Firm*—William J. Mason

[57] ABSTRACT

A process is disclosed for maximizing the growth and nicotine degrading activity of microorganisms effective to degrade nicotine through a biochemical mechanism in which 3-succinoylpyridine is formed. The process involves inoculating a nicotine-containing growth medium with the microorganisms and subjecting the broth to aeration and agitation. During the growth period, the broth should be maintained at a pH of between about 6 and 7.8 and at a temperature between about 10° C and about 45° C. The broth should have an initial nicotine concentration of at least 0.5 mg. per ml. up to an amount which is toxic to the microorganisms.

13 Claims, 1 Drawing Figure

PROCESS FOR MAXIMIZING THE GROWTH AND NICOTINE DEGRADING ACTIVITY OF MICROORGANISMS

FIELD OF INVENTION

The present invention pertains to a process for maximizing the growth and nicotine degrading activity of microorganisms used for treating tobacco to reduce its nicotine content. More specifically, the present invention pertains to a process for growing certain microorganisms, in a nicotine containing broth, under controlled conditions, whereby microorganism growth and nicotine degrading activity is maximized.

BACKGROUND OF THE INVENTION

For various reasons, it is often desirable to reduce the nicotine content of tobacco. For example, in recent years, low nicotine content "mild" cigarettes have gained substantial consumer acceptance.

There are numerous techniques available for reducing the nicotine content of tobacco. However, most of these techniques result in the removal of other tobacco ingredients along with the nicotine. The removal of other ingredients adversely affects desirable flavor and taste properties, or other desirable smoking qualities. Thus, there is a need for techniques which are effective to selectively reduce the nicotine content of tobacco without deleteriously modifying its desirable smoking properties.

Processes for the reduction of the nicotine content of tobacco by microbial treatment are disclosed in copending applications Ser. No. 632,804 filed Nov. 17, 1975, by Geiss, et al. and Ser. No. 632,863 filed Nov. 17, 1975, by Newton, et al.

The microbial treatments of these copending applications, which are incorporated herein by reference, involve the use of microorganism cultures which are specific to nicotine whereby the nicotine content of tobacco may be substantially reduced without producing any substantial effect on other components of the tobacco. While the nicotine content of tobacco is reduced by these processes, the organoleptic properties attributed to smoke generated from the tobacco are generally maintained. However, after treatment, a milder smoke is produced.

The process of the present invention provides a technique for maximizing the growth and nicotine degrading activity of microorganisms useful for treating tobacco to reduce the nicotine content thereof. The microorganisms suitable for use in the present invention are those which degrade nicotine through a biochemical reaction in which 3-succinoylpyridine, as well as 6-hydroxy-3-succinoylpyridine and other by-products, are formed. After cultures of the microorganisms are prepared in accordance with the process of the present invention, they may be employed to reduce the nicotine content of tobacco by inoculating tobacco with the cultures under proper conditions of temperature, moisture and pH.

SUMMARY OF THE INVENTION

The present invention, which provides a process for maximizing the growth and nicotine degrading activity of certain microorganisms, involves inoculating a nicotine-containing broth with the microorganisms and subjecting the broth to aeration and agitation. The microorganisms grown by the process of the present invention are those effective to degrade nicotine through a biochemical mechanism in which 3-succinoylpyridine is formed. Suitable microorganisms are selected from the group consisting of *Cellulomonas sp.* and *Pseudomonas putida.*

During the period in which the culture of microorganisms is grown in the broth, the broth is maintained at a pH of between about 6 and about 7.8, while the temperature is maintained between about 10° C and about 45° C. The broth should have an initial nicotine concentration of at least 0.5 mg. per ml. of nicotine up to an amount which is toxic to the microorganisms.

The microorganism culture exhibits maximum nicotine degrading activity after the time the culture exhibits maximum oxygen demand and maximum carbon dioxide evolution, but prior to the time after these maxima that the culture exhibits minimum oxygen demand and minimum carbon dioxide evolution. For this reason, preferably the culture is applied to tobacco after the maxima have been observed but prior to subsequent minimum oxygen demand and minimum carbon dioxide evolution.

DESCRIPTION OF THE PREFERRED EMBODIMENTS

Pure culture isolates of bacteria effective in degrading nicotine through a biochemical mechanism in which 3-succinoylpyridine is formed, which are suitable for treating tobacco to reduce its nicotine content, can be obtained by culture enrichment techniques. Three bacterial species, of the type which may be suitably grown by the process of the present invention, have been obtained from cigar tobacco.

Puerto Rican cigar tobacco (500 grams) was adjusted to an 80% moisture level with water, bulked tightly, enclosed in plastic, and allowed to incubate over night at approximately 25° C. Sampling for alkaloids in the tobacco and rebulking took place after 18 hours. The incubation and rebulking cycle continued for a few days until the alkaloid level in the tobacco was very low.

After a few days, 5 grams of the treated cigar tobacco was added to a flask of a nutrient containing nicotine broth and incubated at 30° C with shaking. The nicotine broth comprised 0.02 g. $FeSO_4$, 4 ml. nicotine, 2.0 g. $KH_2PO_4$, 5.0 g. KCl, 0.2 g. $MgSO_4$, 0.1 g. yeast extract, and 1 liter of water to make a broth having a pH of 6.8.

Subsequent alkaloid analysis of the nicotine broth showed that the nicotine was decomposed. Nicotine was added to the broth to return the nicotine level to 4 mg./ml. This in turn was depleted. Fresh nicotine broth was inoculated Fresh media with additional nicotine were used through several successive transfers.

Materials from the flasks of inoculated nicotine broth were streaked on nicotine agar, having the same composition as the nutrient containing nicotine broth, except for the addition of 1.5% agar, and incubated at 30° C. The most vigorous colonies of bacteria which developed on the nicotine agar were restreaked several times to obtained pure strains.

From the original colonies, three strains of bacteria were obtained, identified, and deposited with the U.S.

Department of Agriculture (at the Northern Regional Research Laboratory, Peoria, Ill.). One strain, referred to herein as isolate *Cellulomonas sp.* (NRRL B-8063), had irregular colonies. Another referred to herein as isolate *Pseudomonas putida* (NRRL B-8062), had smooth milky colonies, and the third, referred to herein as isolate *Pseudomonas putida* (NRRL B-8061), had smooth white colonies.

Strains NRRL B-8061 and NRRL B-8062 ) show a more aggressive nicotine degrading tendency than strain NRRL B-8063. *Pseudomonas putida* (NRRL B-8061) is the preferred microorganism for use in the process of the present invention, although *Pseudomonas putida* (NRRL B-8062) is very similar in most capabilities. The morphological and biochemical characteristics of *Pseudomonas putida* (NRRL B-8061 and NRRL B-8062) and *Cellulomonas sp.* (NRRL B-8063) are shown in Tables I, II and III, respectively.

TABLE I

MORPHOLOGICAL AND BIOCHEMICAL CHARACTERISTICS OF *PSEUDOMONAS PUTIDA* (NRRL B-8061)

A. MORPHOLOGY

Rods, oval to short in shape, 0.8–1.0 microns (diameter) by 1.0–2.2 microns (length); predominantly coccoidal. Form pairs and longer filaments.

Colony Form:
 Nutrient Agar: Opalescent, light tan or cream colored, flat smooth edges.
 Peptone Yeast Extract Agar: Appearance much like that on Nutrient Agar; accompanied by the formation of a diffusible yellow pigment which fluoresces under ultraviolet light. This pigment produced well in media with glucose present.
 Nicotine Agar: Filiform, opaque, pearl-gray, butyrous, glistening.
 Brain Heart Infusion Agar: Circular, umbonate, rugose, undulate, glistening, opaque, pearl-gray.
 Growth type in static Brain Heart Infusion Broth: Turbid, membranous surface growth, flocculent sediment, heavy growth.
 Gram negative
 Motile by three or more polar flagella.

B. PHYSIOLOGY

Obligate aerobe. Strongly aerotactic.
Optimum growth: 25°–30° C. Range: 12°–37° C.
Nitrate reduced to nitrite, no gas formed.
Tellurite Reduction: negative.
Growth with Benzoic acid as substrate. Growth with citrate as sole carbon source, forming fluorescent yellow pigment.
No growth on trehalose, or with mandelic acid, 2-hydroxypyridine or pyridine.
Hydrolysis of arginine, positive. Gelatin, starch, cellulose, casein and urea not hydrolyzed.
 Lactic acid produced.
 Oxidase produced.
 Ammonia produced.
 Acid and hydrogen sulfide not produced.
 Catalase present.
 Acetylmethyl-carbinol and indole not present.
 Litmus milk: Alkaline, then reduced.
 No hemolysis of blood agar.
 Acid but no gas from: Adonitol, arabinose, cellobiose, dulcitol, fructose, galactose, mannose, melibiose, raffinose, rhamnose, salicin.
 Growth with no acid or gas production with lactose, sucrose, maltose, glucose, xylose, dextrin, glycerol, mannitol, and inositol.
 Growth but no phenazine pigment production on Kings medium A. Growth and fluorescent pigment on Kings medium B.
 Grows with nicotine and nicotinic acid as sole sources of carbon. Ultraviolet spectrum of the growth liquid at time of pigmentation shows accumulation of 2, 5-dihydroxypyridine with both substrates.

GC ratio: Melting point method: 62.5. CsCl density gradient centrifugation: 63.2.

Pathogenicity: Non-pathogenic to guinea pigs when fed orally or injected intraperitoneally.

Source: Tobacco.

TABLE II

MORPHOLOGICAL AND BIOCHEMICAL CHARACTERISTICS OF *PSEUDOMONAS PUTIDA* (NRRL B-8062)

A. MORPHOLOGY

Rods, oval to short in shape, 0.8–1.0 microns (diameter) by 1.0–2.2 microns (length); predominantly coccoidal. Form pairs and longer filaments.

Colony Form:
 Nutrient Agar: Opalescent, light tan or cream colored, flat smooth edges.
 Peptone Yeast Extract Agar: Appearance much like that on Nutrient Agar; accompanied by the formation of a diffusible yellow pigment which fluoresces under ultraviolet light. This pigment produced well in media with glucose present.
 Nicotine Agar: Filiform, opaque, pearl-gray, butyrous, glistening.
 Brain Heart Infusion Agar: Circular, umbonate, rugose, undulate, glistening, opaque, pearl-gray.
 Growth type in static Brain Heart Infusion Broth: Turbid, membranous surface growth, flocculent sediment, heavy growth.
 Gram negative.
 Motile by three or more polar flagella.

B. PHYSIOLOGY

Obligate aerobe. Strongly aerotactic.
Optimum growth: 25°–30° C. Range: 12°–37° C.
Nitrate reduced to nitrite, no gas formed.
Tellurite Reduction: negative.
Growth with Benzoic acid as substrate. Growth with citrate as sole carbon source, forming fluorescent yellow pigment.
No growth on trehalose, or with mandelic acid, 2-hydroxypyridine or pyridine.
Hydrolysis of arginine, positive. Gelatin, starch, cellulose, casein, and urea not hydrolyzed.
 Lactic acid produced.
 Oxidase produced.
 Ammonia not produced.
 Acid and hydrogen sulfide not produced.
 Catalase present.
 Acetylmethyl-carbinol and indole not present.
 Litmus milk: Alkaline, then reduced.
 No hemolysis of blood agar.
 Acid but no gas form: Adonitol, arabinose, cellobiose, dulcitol, fructose, galactose, mannose, melibiose, raffinose, rhamnose, salicin.
 Growth with no acid or gas production with lactose, sucrose, maltose, glucose, xylose, dextrin, glycerol, mannitol, and inositol.

Growth but no phenazine pigment production on Kings medium.

A. Growth and fluorescent pigment on Kings medium B.

Grows with nicotine and nicotinic acid as sole sources of carbon. Ultraviolet spectrum of the growth liquid at time of pigmentation shows accumulation of 2,5-dihydroxypyridine with both substrates.

GC ratio: Melting point method: 61.0. CsCl density gradient centrifugation: 62.2.

Pathogenicity: Non-pathogenic to guinea pigs when fed orally or injected intraperitoneally.

Source: Tobacco.

TABLE III

MORPPOLOGICAL AND BIOCHEMICAL CHARACTERISTICS OF *CELLULOMONAS SP.* (NRRL B-8063)

A. MORPPOLOGY

Cells are thin, bent or almost vibroid rods with a diameter of 0.5–0.7 microns and length of 1.5–2.5 microns.

Colony Form:
  Nutrient Agar: Small, yellow, flat, butyrous, and with smooth edges.
  Peptone Yeast Extract Agar: Similar appearance to that on nutrient Agar. No exocellular pigments were formed when growing on a variety of media, including nicotine.
  Nicotine Agar: Filiform, opaque, pearl-gray, membranous, dull.
  Brain Heart Infusion Agar: Circular, umbonate, contoured, undulate, dull, opaque, pearl-gray.
  Growth type in static Brain Heart Infusion Broth: Turbid, viscid, ringed, moderate growth.

Gram positive when young, variable as stationary growth is reached.

Motile by tumbling action. Cells possess 1 or 2 polar flagella.

B. PHYSIOLOGY

Facultative anerobe; obligate aerobe when nitrate is present.

Optimum growth: 28°–30° C. Range: 15°–37° C.

Reduces nitrate to nitrite and actively produces nitrogen gas.

Grows with nicotine and benzoic acid as sole carbon sources. No pigment formed. Spectral scans of growth liquor from nicotine showed no evidence of dipyridols.

No growth with mandelic acid, 2-hydroxypyridine, or pyridine.

No hydrolysis of gelatin, starch, cellulose, casein, urea, or arginine.

Grows with citrate as sole carbon source.

Tellurite reduction: negative.

No production of hydrogen sulfide.

Lactic acid, oxidase and ammonia produced.

Catalase, positive.

Indole present, weak.

Acetylmethyl-carbinol not present.

Litmus milk, alkaline, then reduced.

No pigment on Kings A or B medium.

Growth with no acid or gas production on glucose, sucrose, maltose, fructose, galactose, raffinose, xylose, salicin, adonitol, glycerol and inositol.

No growth on lactose.

Acid but no gas from: arabinose, cellobiose, mannose, melibiose, rhamnose, dextrin, dulcitol and mannitol.

No hemolysis of blood agar.

GC ratio: Melting point method, 69.2. CsCl density gradient centrifugation, 68.9.

Pathogenicity: Non-pathogenic to guinea pigs when fed orally or injected intraperitoneally.

Source: Tobacco.

Microorganism strains, such as NRRL B-8061, NRRL B-8061, NRRL B-8062 and NRRL B-8063, may be grown by inoculating a nutrient-containing nicotine broth, such as the broth previously described, with the microorganisms. Typically, inoculation involves transferring microorganisms from a nicotine agar slant, such as the nicotine agar slant previously described, to the broth. The inoculated broth is then transferred to a fermentor, such as a New Brunswick Scientific Fermentor (MF-214) equipped with a pH controller and dissolved oxygen monitor.

Prior to transfer to the fermentor, the microorganisms may be allowed to grow in the nutrient containing nicotine broth. Suitable conditions would include a temperature of about 30° C and mild agitation, such as obtained by stirring the broth at about 220 rpm. The microorganisms may be allowed to grow in the broth for, e.g., 22 to 26 hours.

The inoculated nutrient-containing broth may then be transferred to a tobacco extract broth, preferably an extract of burley tobacco, containing from 0.5 mg. per ml. nicotine up to an amount which is toxic to the microorganisms. Preferably, the nicotine concentration is between about 1.5 mg. per ml. and about 12 mg. per ml. Concentrations of nicotine greater than about 12 mg. per ml. normally substantially slow microorganism growth.

In the fermentor, the inoculum is subjected to aeration and agitation. A suitable aeration rate would be between about 0.25 and about 2 volume units of air displacement per minute for each volume unit of broth, and preferably about 1 unit air displacement per minute (e.g., 1 liter air per minute for each 1 liter of broth). Suitable agitation may be obtained by stirring with an impeller at a rate between about 300 rpm and 900 rpm, preferably about 600 rpm.

Although the microorganisms can be easily grown with varying combinations of aeration and agitation, there are disadvantages to some combinations. For example, an aeration rate of significantly lower than 0.25 units air displacement per minute does not supply the oxygen requirement for rapid culture growth, while a greater air movement than about 2 units air displacement per minute either is unneeded or causes excessive foam formation. Foam formation entails additional control and potential contamination problems. Similar problems hold true for agitation rates lesser than about 300 rpm and greater than about 900 rpm.

Aeration of the burley extract growth medium may lead to foam formation during microorganism growth. Accordingly, it is advantageous to add an antifoam compound to the broth. A commercial polyglycol antifoam known as Dow Corning P-1200, a polyglycol having an average molecular weight of 1200 and a viscosity at 100° F of 93.1 centistokes, may be advantageously employed.

During culture growth, the pH should be controlled so that it is maintained between about 6 and about 7.8. The microorganisms will grow and develop good nicotine degrading activity throughout this entire range. However, it is preferred to control the pH between about 6.7 and about 7.2. A target pH of 7 is particularly advantageous, as utilizing a pH control at about 7 lends flexibility either up or down should it become necessary during inoculum development. Attempting to control pH at 6 or 7.8 allows little downward or upward flexibility, since the culture will not grow and develop good nicotine degrading activity at pH levels outside this range. Hydrochloric acid and sodium hydroxide, such as 2N HCl and 2N NaOH, may be used for controlling the pH.

A culture can be grown without strict pH control and used successfully to treat tobacco. However, without control the pH naturally shifts upward towards 8 or above. Growth at a constant pH of 8 or above dramatically inhibits culture development and activity If, during incubation, the pH is allowed to reach 8 and remain there, microorganism activity is very difficult to recover.

During the growth of the culture of microorganisms variations in temperature are acceptable, but over extended growth periods the temperature should be maintained between about 10° C and about 45° C, and preferably between about 28° C and 32° C. At temperatures below 10° C, growth is very slow and temperatures above 45° C tend to be harmful to the microorganisms. Once prepared, cultures can be held at refrigeration temperatures prior to use on tobacco without deleterious effect on the microorganisms.

While the amount of inoculum employed is in no way critical, the culture preparation time is dependent upon the amount of microorganism employed to inoculate the nicotine-containing broth. Inoculating the nicotine-containing broth with about 1% to about 10% (preferably about 5%) by volume of an inoculum containing between about $1 \times 10^9$ and $3 \times 10^9$ cells per ml. will provide a culture with good tobacco nicotine degrading activity in approximately 6.5 hours.

To obtain good growth and nicotine degrading activity, the nicotine-containing broth should have an initial nicotine concentration of at least 0.5 mg. per ml. Generally, higher initial alkaloid levels in the broth produce a larger cell count by the time the microorganism has reached its point of maximum activity. However, for a given inoculum rate, higher initial alkaloid levels require a longer incubation period to reach maximum acitivity.

The nicotine degrading culture which may be grown by the process of the present invention more rapidly reaches maximum nicotine degrading activity in a process of sequential inoculum development. Specifically, if a nicotine-containing broth is inoculated with microorganisms which were grown by the process of the present invention, and then the microorganisms are again grown by the process of the present invention, the culture of the second growth process will reach maximum nicotine degrading activity faster than that of the first growth process, assuming that the microorganisms used to inoculate the broth of the first growth process were not grown under the conditions of the present invention. This phenomenon is believed due to (1) greater initial cell mass with inoculum grown by the process of the present invention, and (2) enhanced enzyme activity of the culture grown by the process of the present invention.

There are two features of the culture growth in the nicotine-containing broth that are direct indicators of the microorganism's nicotine degrading activity. These are oxygen usage and carbon dioxide evolution. The oxygen demand and carbon dioxide evolution may be readily monitored as a technique for determining the readiness of the culture for application to tobacco.

Figure 1:
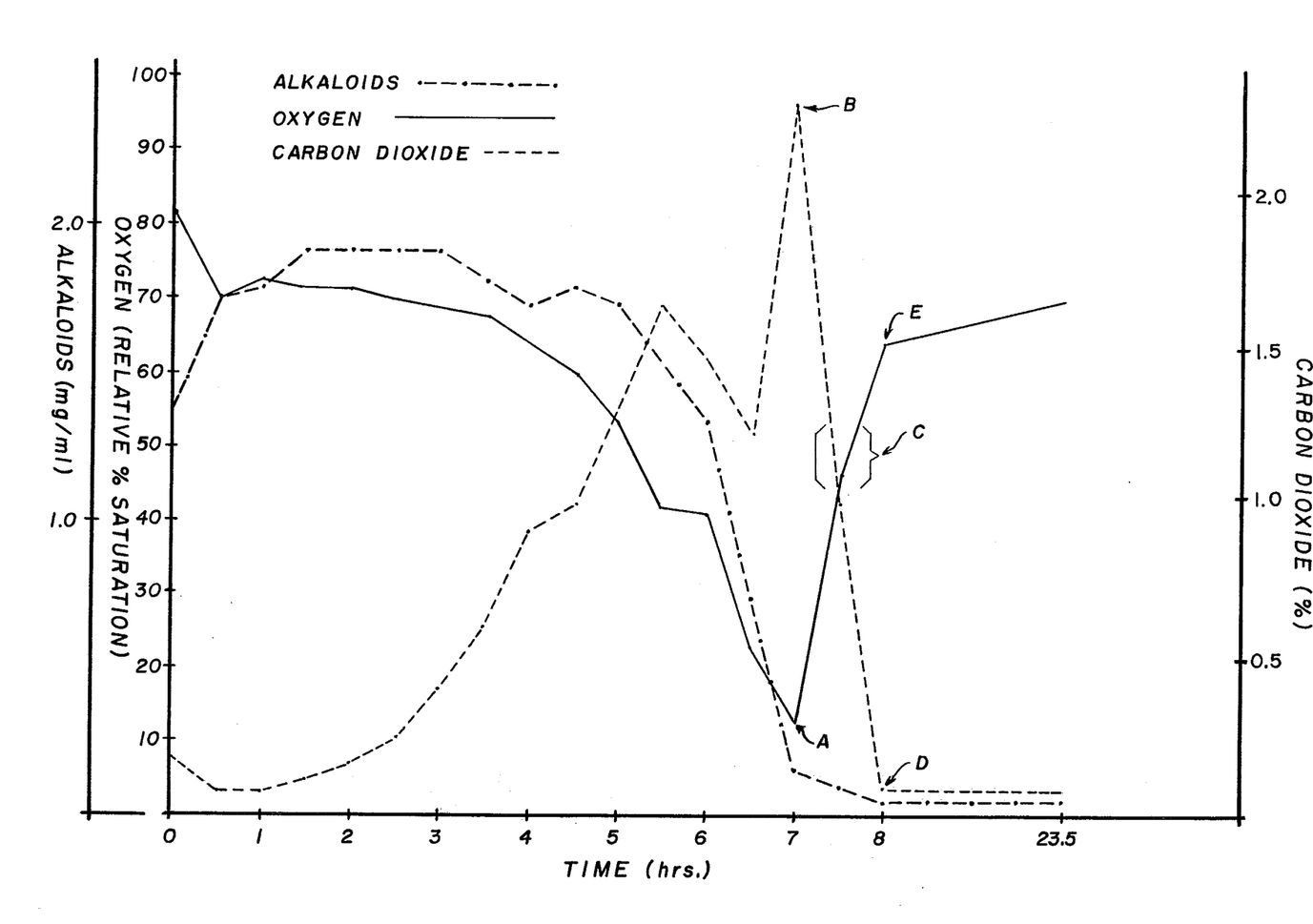
The FIG. is a plot illustrating oxygen usage and carbon dioxide evolution, as well as alkaloid degradation, for culture growth in a nicotine containing broth.

The figure is a plot of oxygen usage (in terms of relative percent saturation of dissolved oxygen in the system) and carbon dioxide evolution (in terms of percent $CO_2$ in the effluent air stream) for microorganisms grown in 8 liters of a burley blend broth. The alkaloid concentration of the broth is also plotted in the figure.

The broth contains an initial nicotine concentration of about 2 mg. per ml. and was inoculated with 3% by volume of an inoculum which had been grown for 22 hours in a nutrient-containing nicotine broth of the type previously described. The culture was grown at 30° C in a broth which was subjected to agitation by an impeller set at 600 rpm. Air was introduced into the broth at the rate of 8 liters per min and the pH was regulated, using 2N and 1N NaOH.

The maximum nicotine degrading activity is obtained as the alkaloid concentration in the broth approaches approximately 0.2 mg./ml. This point is coincident with a time after the culture has exhibited maximum oxygen demand and maximum carbon dioxide evolution, but prior to the time following this poit that the carbon dioxide evolution and oxygen demand reach minimums.

With specific reference to the FIGURE, the time of maximum oxygen demand is shown as point A. There is a parallel carbon dioxide evolution maximum which is shown as point B. These maxima immediately precede the point of maximum culture nicotine degrading activity. At a subsequent time when the carbon dioxide evolution minimizes (point D) and the oxygen demand minimizes, or ceases to rapidly decrease (point E) the time of maximum nicotine degrading activity has passed. The optimum nicotine degrading activity is obtained in the area noted on the plot as "C."

The process of the present invention may be further illustrated by the following specific examples. The examples are intended merely to illustrate specific embodiments, and are in no way limiting.

EXAMPLE 1

PREPARATION OF INOCULUM
Nicotine Agar and Broth

Nicotine agar was prepared according to the following formula:

| | | |
|---|---|---|
| Nicotine | 4.0 | ml. |
| $FeSO_4$ | 0.025 | gm. |
| $KH_2PO_4$ | 2.0 | gm. |
| KCl | 5.0 | gm. |
| $MgSO_4$ | 0.25 | gm. |
| Yeast Extract | 0.1 | gm. |
| Agar | 15.0 | gm. |
| Distilled or Deionized Water | To make 1 liter | |
| Final pH 6.8 | | |

The medium is sterilized in an autoclave for 15 minutes at 15 psig and 121° C. Nicotine is usually added to the medium just prior to use. A broth of the above medium is prepared by omitting the addition of agar.

Tobacco-Nicotine Broth

An extract of burley tobacco is prepared as follows: 100 grams of burley tobacco is mixed with 1000 mls of water and cooked in an autoclave for 25 minutes at 15 psig and 121° C. The resultant effluent liquor is removed and the volume adjusted to the original amount. An equal volume of an aqueous broth containing 0.05 gm. $FeSO_4$, 4.0 gm. $KH_2PO_4$, 10.0 gm. KCl, 0.5 gm. $MgSO_4$, and 0.2 gm. yeast extract is added to the burley tobacco extract. The medium is sterilized in an autoclave for 15 minutes at 15 psig and 121° C. Just prior to use, nicotine is added to give a final nicotine concentration of 4.0 mg./ml. Flue-cured tobacco can be used successfully in this medium in place of burley tobacco.

Tobacco Extract Broth

Tobacco extract broth is prepared in the same manner as the burley extract used in the tobacco-nicotine broth. Water may or may not be added, depending upon the final nicotine concentration desired.

The microorganisms where grown in the burley tobacco extract broth at 30° C under varying conditions of aeration and agitation. Three batches were subjected to forced air and agitation at rates of, respectively, 1600 cc per min. and 300 rpm; 4000 cc per min. and 600 rpm; and 4000 cc per min. and 900 rpm. The pH of the batches were regulated using HCl and NaOH. The results of this test are set forth in Table IV.

As is apparent from the data in Table IV, most rapid growth was achieved using a high rate of agitation (900 rpm) and a low rate of aeration (4000 cc per min.). However, agitating at 900 rpm tended to cause the formation of substantial amounts of foam. Thus, moderate aeration (8000 cc per min.) and agitation (600 rpm) rates are preferred (See Example 3 and Table V).

TABLE IV

ALKALOID DEGRADATION UNDER VARIOUS COMBINATIONS OF AERATION/AGITATION

| Aeration (cc/min) | 16,000 | | | | 4,000 | | | | 4,000 | | | |
|---|---|---|---|---|---|---|---|---|---|---|---|---|
| Agitation (rpm) | 300 | | | | 600 | | | | 900 | | | |
| Sample Description | Viable Count (cells/ml) ($\times 10^5$) | Alkaloids (mg/ml) | Dissolved $O_2$ (% Relative) | pH | Viable Count (cells/ml) ($\times 10^6$) | Alkaloids (mg/ml) | Dissolved $O_2$ (% Relative) | pH | Viable Count (cells/ml) (X106) | Alkaloids (mg/ml) | Dissolved $O_2$ (% Relative) | pH |
| Before Inoculation | — | 1.87 | 100 | 7.2 | — | 1.65 | 82 | 7.88 | — | 2.11 | 72 | 5.6 |
| Inoculum | 2,100 | 0.14 | — | 7.5 | 1,300 | 0.07 | — | 7.39 | 1,670 | 0.14 | — | 7.9 |
| After Inoculation | 6 | 1.69 | 100 | 7.0 | 34 | 1.65 | 84 | 7.28 | 25 | 2.04 | 72 | 6.6 |
| 1 hour after | 21 | 1.72 | 100 | 7.0 | 40 | 1.65 | 88 | 7.26 | 86 | 2.20 | 73 | 7.0 |
| 2 hours after | 20 | 1.67 | 100 | 7.0 | 38 | 1.56 | 88 | 7.17 | 72 | 2.15 | 72 | 7.1 |
| 3 hours after | 34 | 1.65 | 96 | 7.0 | 47 | 1.57 | 86 | 7.18 | 330 | 1.98 | 68 | 7.2 |
| 4 hours after | 84 | 1.65 | 80 | 7.0 | 147 | 1.57 | 81 | 7.19 | 1,010 | 1.76 | 60 | 7.5 |
| 5 hours after | 370 | 1.54 | 44 | 7.0 | 500 | 1.57 | 70 | 7.17 | 2,400 | 1.76 | 47 | 7.6 |
| 6 hours after | 960 | — | 18 | 7.0 | 690 | 1.46 | 64 | 7.16 | 3,400 | 1.80 | 40 | 7.6 |
| 7 hours after | — | 1.76 | 12 | 7.0 | 3,100 | 1.33 | 47 | 7.40 | 6,600 | 0.55 | 34 | 7.7 |
| 7.5 hours after | — | — | — | 7.0 | | 1.27 | 36 | 7.60 | 9,200 | 0.1 | 70 | 7.7 |
| 8 hours after | 2.110 | 1.21 | 6 | 7.0 | | | | | | | | |
| 9 hours after | 2,700 | 0.77 | 5 | 7.0 | | | | | | | | |
| 10 hours after | 3,600 | 0.26 | 6 | 7.0 | | | | | | | | |
| 11 hours after | 3,330 | 0.18 | 4 | 7.0 | | | | | | | | |
| 22 hours after | — | | — | 7.0 | | 0.98 | 80 | 6.9 | | | | |

Broth Inoculation

The microorganisms, such as strain NRRL B-8061, are incubated on agar slants for 25 to 72 hours at 30° C. Liquid media, for example tobacco-nicotine broth, are inoculated with a sterile water wash from slants which has been diluted to an optical density of 0.5 as read at 650 mu on a spectrophotometer (B&L Spectronic 20). A 1% (v/v) inoculum rate of the standardized suspension is added to one of the broth media for culture propagation. Growth is enhanced by employing rotary agitation for 24 to 48 hours at 30° C and 220 rpm.

EXAMPLE 2

To illustrate the effect of aeration and agitation, a tobacco-nicotine broth of the type described in Example 1 was inoculated with P. putida (NRRL B-8061) by means of a sterile water wash from nicotine agar slants of the type described in Example 1.

After being maintained for 24 hours at 30° C, the tobacco-nicotine broth was used to inoculate separate 8 liter batches of burley tobacco extract broth (described in Example 1) in New Brunswick Scientific Fermentors (MF-214). The burley tobacco extract broth was inoculated with 3% by volume of the tobacco-nicotine broth.

EXAMPLE 3

To illustrate the importance of pH control, P. putida (NRRL B-8061) was grown, using the technique of Example II, in two batches of 8 liters of a burley nicotine extract broth subjected to aeration by forced air at a rate of 8000 cc per min. and agitation at 600 rpm. In one batch, no effort was made to control the pH, while in the other batch an effort was made to control the pH, with 1N HCl, and 2N NaOH, at 7.0.

Because of the strong tendency of the microorganism to produce basic components, causing a shift in the burley tobacco extract broth towards a pH of 8, it was not possible to control the pH at a constant 7.0. However, in the pH controlled batch, it was possible to keep the pH below 8 and any upward shifts in the pH did not last long enough to destroy the tobacco nicotine degrading activity of the microorganism. Results of this test are reported in Table V.

At various times during growth of the microorganisms, portions of the culture were removed and applied to tobacco. The tobacco was then bulked for 16 hours. As further shown by the data of Table V, the pH controlled batch had greatly enhanced tobacco nicotine degrading activity. This difference is particularly pronounced with respect to the two batches of microorganisms which were grown for 7 hours.

TABLE V

GROWTH AND ALKALOID DEGRADATION IN pH CONTROLLED AND UNCONTROLLED BROTHS

| Sample Description | Viable Count (cells/ml) ($\times 10^6$) | | Alkaloids (mg/ml) | | pH | | Alkaloids in Tobacco After 16 Hrs. Treatment | |
|---|---|---|---|---|---|---|---|---|
| | pH Control | No pH Control | pH Control | No pH Control | Control | No Control | pH Control | No pH Control |
| Before Inoculation | — | — | 2.09 | 1.89 | 5.8 | 5.8 | | |
| Inoculum | 1,280 | 1,280 | 0.14 | 0.14 | 7.8 | 7.8 | | |
| 0 hours after | 24 | 23 | 1.98 | 1.87 | 6.0 | 5.88 | 3.29 | 3.65 |
| 1 hour after | 27 | 29 | 1.98 | 2.09 | 6.6 | 5.97 | | |
| 2 hours after | 65 | 49 | 1.87 | 1.98 | 7.0 | 6.11 | | |
| 3 hours after | 143 | 138 | 1.95 | 1.87 | 7.0 | 6.39 | | |
| 4 hours after | 500 | 580 | 1.65 | 1.78 | 7.2 | 7.23 | | |
| 5 hours after | 2,200 | 1,820 | — | — | 7.6 | 7.87 | 2.83 | 3.35 |
| 6 hours after | 3,700 | 2,100 | 1.43 | 1.76 | 7.8 | 8.07 | | |
| 6.5 hours after | — | — | 1.27 | 1.67 | 7.9 | — | | |
| 7 hours after | 5,600 | 3,400 | 0.66 | 1.37 | 7.9 | 8.16 | 0.93 | 2.40 |
| 7.5 hours after | — | — | 0.33 | 1.27 | 7.85 | — | | |

At longer growth times, the microorganism in either the pH controlled batch or the non-pH controlled batch tended to lose its nicotine tobacco degrading activity. However, in the pH controlled batch, it was possible to restore the tobacco nicotine degrading activity by adding fresh nicotine to the broth. In the batch where the pH had not been controlled, it was not possible to restore nicotine degrading activity by adding fresh nicotine to the batch.

EXAMPLE 4

To illustrate the effect of initial alkaloid level in the growth medium, four batches of microorganisms were grown generally following the technique of Example II. In each of the tests, 8 liters of a burley tobacco extract broth were inoculated with 5% by volume of the tobacco-nicotine broth containing approximately $2 \times 10^9$ cells per ml. in fermentors stirred at a rate of 600 rpm and subjected to forced aeration at the rate of 8000 cc per in. In each instance, the temperature was controlled at approximately 30° C and the pH was regulated as nearly as possible to 7.0. The results of this test are set forth in Table VI. The initial alkaloid levels of the growth media are set forth in the Table.

As is apparent from the data of Table VI, the higher the initial alkaloid level, the longer it takes for the cultures to develop their maximum nicotine degrading potential. However, there is a minimum time required to develop a strong enzyme activity regardless of initial alkaloid level.

TABLE VI

EFFECT OF INITIAL ALKALOID LEVEL ON INOCULUM PREPARATON TIME

| Sample Description | Alkaloid (mg/ml) | | | |
|---|---|---|---|---|
| | Level 1 | Level 2 | Level 3 | Level 4 |
| Before inoculation | 0.81 | 1.84 | 2.28 | 3.18 |
| Inoculum | 0.14 | 0.07 | 0.05 | 0.07 |
| After Inoculation | 0.68 | 1.45 | 2.24 | 2.92 |
| 1 hour after | 0.58 | 1.40 | 2.10 | 2.66 |
| 2 hours after | 0.38 | 1.50 | 2.04 | 2.77 |
| 3 hours after | 0.38 | 1.44 | 1.92 | 2.77 |
| 4 hours after | 0.19 | 1.28 | 1.81 | 2.65 |
| 5 hours after | 0.08 | 1.14 | 1.54 | 2.47 |
| 5.5 hours after | 0.05 | 0.79 | 0.94 | 2.26 |
| 6 hours after | — | 0.30 | — | — |
| 6.5 hours after | — | 0.13 | 0.38 | — |
| 7 hours after | — | — | 0.21 | 1.22 |

EXAMPLE 5

To illustrate that P. putida (NRRL B-8061) develops more rapidly in sequential development, the microorganism was grown in two stages. In the first stage, the microorganism was grown essentially following the technique of Example 2, except that 8 liters of the burley tobacco extract broth were inoculated with 5% by volume of the tobacco-nicotine broth and the burley extract broth was subjected to agitation at 600 rpm and aeration at the rate of 8000 cc air per min. at 30° C.

After 7 hours growth a portion of the burley extract blend was removed from the fermentor and used as an inoculum for the second fermentor stage. The second stage was inoculated with 5% by volume of the burley tobacco extract from the first stage and grown under identical conditions to those employed in the first stage. As the data in Table VII demonstrates, higher cell concentrations are obtained during the second stage.

Those skilled in the art will visualize that many modifications and variations may be made in the invention set forth without departing from its spirit and scope. Accordingly, while preferred embodiments of the invention have been described, it is understood that the invention is not confined to the species set forth by way of illustration.

TABLE VII

PATTERN OF ALKALOID CHANGE IN TWO STAGE FERMENTOR INOCULUM DEVELOPMENT

| | Stage 1 | | | | Stage 2 | | | |
|---|---|---|---|---|---|---|---|---|
| Sample Description | Viable Count (cells/ml) ($\times 10^6$) | Akaloid (mg/ml) | pH | Dissolved Oxygen (% Relative) | Viable Count (cells/ml) ($\times 10^6$) | Alkaloid (mg/ml) | Oxygen pH | Dissolved (% Relative) |
| Before inoculation | — | 2.46 | 6.0 | 56 | — | 2.16 | 6.8 | 60 |
| Inoculum | 2,600 | 0.07 | 7.5 | — | 5,700 | 0.13 | 8.11 | — |
| After inoculaton | 72 | 2.17 | 7.0 | 56 | 500 | 2.16 | 7.0 | 60 |
| 1 hour after | 116 | 1.99 | 7.0 | 58 | 530 | 2.06 | 7.0 | 50 |
| 2 hours after | 410 | 1.84 | 7.0 | 55 | 2,280 | 1.81 | 7.1 | 44 |
| 3 hours after | 560 | 1.83 | 7.1 | 52 | 2,740 | 1.78 | 7.4 | 28 |

TABLE VII-continued
PATTERN OF ALKALOID CHANGE IN TWO STAGE FERMENTOR INOCULUM DEVELOPMENT

| | Stage 1 | | | | Stage 2 | | | |
|---|---|---|---|---|---|---|---|---|
| Sample Description | Viable Count (cells/ml) (X10⁶) | Akaloid (mg/ml) | pH | Dissolved Oxygen (% Relative) | Viable Count (cells/ml) (X10⁶) | Alkaloid (mg/ml) | Oxygen pH | Dissolved (% Relative) |
| 4 hours after | 1,230 | 1.84 | 7.1 | 40 | 3,920 | 1.35 | 7.5 | 6 |
| 4.5 hours after | — | — | — | — | 5,100 | 0.79 | 7.6 | 6 |
| 5 hours after | 1,760 | 1.62 | 7.3 | 20 | — | 0.18 | 7.6 | 24 |
| 5.5 hours after | 3,400 | 1.27 | 7.4 | 22 | 17,300 | 0.14 | 7.8 | 44 |
| 6 hours after | 3,000 | 0.72 | 7.4 | 8 | — | 0.12 | 7.7 | 46 |
| 6.5 hours after | — | — | 7.4 | 40 | — | — | — | — |
| 7 hours after | 5,700 | 0.126 | 7.6 | 51 | — | — | — | — |

What is claimed is:

1. The process of maximizing the growth and nicotine degrading activity of microorganisms effective to degrade nicotine through a biochemical mechanism in which 3-succinoylpyridine is formed, which microorganisms are selected from the group consisting of *Cellulomonas sp.* and *Pseudomonas putida*, comprising:
   inoculating nicotine containing broth with said microorganisms, and
   subjecting said broth to aeration and agitation, said broth:
   a. being maintained at a pH of between about 6 and about 7.8;
   b. having an initial nicotine concentration of at least 0.5 mg. per ml. up to an amount which is toxic to said microorganisms; and
   c. being maintained at a temperature between about 10° C and about 45° C.

2. The process of claim 1 in which said broth is a tobacco extract broth having an initial nicotine concentration of between about 1.5 mg. per ml. and about 12 mg. per ml.

3. The process of claim 2 in which said broth has an initial pH of between about 6.7 and about 7.2 and is maintained at a temperature between about 28° C and 32° C.

4. The process of claim 3 in which said broth is subjected to aeration at a rate of between about 0.25 and about 2 volume units of air displacement per minute for each volume unit of broth.

5. The process of claim 4 in which said broth is subject to agitation by stirring at a rate of between 300 rpm and 900 rpm.

6. The process of claim 1 in which a portion of the inoculated broth is removed after a suitable growth period and used to inoculate a second nicotine containing broth.

7. The process of claim 6 in which said second nicotine containing broth is subjected to aeration and agitation, which broth has an initial nicotine concentration of at least 0.5 mg. per ml. up to an amount which is toxic to the microorganism.

8. The process of claim 7 in which said second nicotine containing broth is maintained at a pH of between 6 and 7.8 and a temperature between about 10° and about 45° C.

9. The process of claim 1 in which said broth inoculated with said microorganisms is applied to tobacco after the time the culture has exhibited maximum oxygen demand and maximum carbon dioxide evolution, but prior to the time after exhibiting maximum oxygen demand and maximum carbon dioxide evolution that the culture exhibits minimum oxygen demand and minimum carbon dioxide evolution.

10. The process of claim 2 in which said broth is a burley tobacco extract broth.

11. The process of claim 10 in which said broth has an initial pH of between about 6.7 and about 7.2 and is maintained at a temperature between about 28° and 32° C.

12. The process of claim 11 in which said broth is subjected to aeration at a rate of between about 0.25 and about 2 volume units of air displacement per minute for each volume unit of broth.

13. The process of claim 12 in which said broth is subject to agitation by stirring at a rate of between 300 rpm and 900 rpm.

* * * * *

UNITED STATES PATENT OFFICE
CERTIFICATE OF CORRECTION

Patent No. 4,011,141     Dated March 8, 1977

Inventor(s) Lawrence E. Gravely, Vernon L. Geiss, Richard P. Newton

It is certified that error appears in the above-identified patent and that said Letters Patent are hereby corrected as shown below:

Column 2, line 58, after "inoculated" insert --from the first flask and again, nicotine depletion occurred.--.

Column 3, line 9, delete ")".
Column 5, line 42, after "is" insert -- not --.
Column 6, line 11, delete "NRRL B-8061".

Column 8, line 20, after "2N" insert --HCl--.

Column 8, line 26, change "poit" to --point--.

Table IV, the figure on the line "8 hours after" under column entitled "Viable Count (cells/ml) ($X10^5$)" should be changed from "2.110" to --2,110--.

Table IV, the figure on the line "11 hours after" under column entitled "Viable Count (cells/ml) ($X10^5$)" should be changed from "3,330" to --3,300--.

Column 11, line 37, change "in." to --min.--.

Table VI, the figure on the line "7 hours after" under column entitled "Level 3" should be changed from "0.21" to --0.12--.

UNITED STATES PATENT OFFICE
CERTIFICATE OF CORRECTION

Patent No. 4,011,141  Dated March 8, 1977

Inventor(s) Lawrence E. Gravely, Vernon L. Geiss, Richard P. Newton

It is certified that error appears in the above-identified patent and that said Letters Patent are hereby corrected as shown below:

Table VII, the column entitled "Oxygen pH" should be entitled --pH--.

Table VII, the column entitled "Dissolved (% Relative)" should read --Dissolved Oxygen (% Relative)--.

Signed and Sealed this

Fourteenth Day of June 1977

[SEAL]

Attest:

RUTH C. MASON
*Attesting Officer*

C. MARSHALL DANN
*Commissioner of Patents and Trademarks*